United States Patent [19]

Stahl

[11] Patent Number: 5,071,427
[45] Date of Patent: Dec. 10, 1991

[54] SURGICAL KNIFE ASSEMBLY INCLUDING DEPTH GUARD

[76] Inventor: Norman O. Stahl, 3199 Monterey Dr., Merrick, N.Y. 11566

[21] Appl. No.: 475,110
[22] Filed: Feb. 5, 1990
[51] Int. Cl.⁵ .............................................. A61B 17/32
[52] U.S. Cl. ...................................... 606/172; 30/293; 30/294
[58] Field of Search ................ 606/166, 167, 172, 177; 30/293, 294, 275

[56] References Cited

U.S. PATENT DOCUMENTS

| | | | |
|---|---|---|---|
| 2,567,102 | 9/1951 | Cook | 30/294 |
| 4,026,295 | 5/1977 | Lieberman . | |
| 4,081,907 | 4/1978 | Bosshold | 30/294 |
| 4,473,076 | 9/1984 | Williams et al. . | |
| 4,494,542 | 1/1985 | Lee . | |
| 4,499,898 | 2/1985 | Knepshield et al. . | |
| 4,520,156 | 6/1985 | Marinoff . | |
| 4,563,815 | 1/1986 | Hoffelner | 30/294 X |
| 4,602,630 | 7/1986 | Anis . | |

FOREIGN PATENT DOCUMENTS 1335263  9/1987  U.S.S.R. ............................. 606/167

Primary Examiner—Michael H. Thaler
Attorney, Agent, or Firm—Hoffmann & Baron

[57] ABSTRACT

A surgical knife assembly is provided which includes a depth guard for limiting the depth of insertion of a cutting blade. The depth guard is constructed to allow a surgeon to view an incision as it is being made. It includes a pair of parallel ski members which define a slot therebetween. A knife blade extends through the slot and includes a cutting edge projecting beyond the respective bottom ends of the ski members. One ski member includes a front edge which allows the front edge of the knife blade to be viewed as an incision is made, while the other ski member extends beyond the front edge of the knife blade to provide stability.

11 Claims, 1 Drawing Sheet

SURGICAL KNIFE ASSEMBLY INCLUDING DEPTH GUARD

BACKGROUND OF THE INVENTION

1. Field of the Invention

The field of the invention relates to surgical knife assemblies including depth guards for limiting the depth of incision of a cutting blade.

2. Brief Description of the Prior Art

It is important to control the depth of incision of a surgical knife blade during an operation. This is particularly important during eye surgery, and a number of devices having been developed for this particular application. U.S. Pat. Nos. 4,473,076, 4,499,898, 4,520,815 and 4,602,630 disclose various cutting instruments for use in eye surgery which include means for limiting the depth of incision of a surgical knife blade.

A conventional instrument known to the art comprises a footplate including a single plate or a pair of parallel plates separated from each other and defining a slot for receiving the knife blade. The footplate includes a flat bottom surface which rests upon the outer surface of the eye as an incision is made, thereby limiting the depth of incision of the blade. One of the problems with this conventional instrument is that the surgeon's field of view is obscured by the plates during the period the incision is made. This is especially true when surgery is performed using a microscope, as the surgeon will then attempt to view the incision from the side of the knife blade.

SUMMARY OF THE INVENTION

It is an object of the invention to provide a surgical knife assembly which includes a guide for limiting the depth of an incision.

It is another object of the invention to provide such a surgical knife assembly which allows a surgeon to observe an incision as it is being made.

In accordance with these and other objects of the invention, a surgical knife assembly is provided which comprises a first ski member having a front end, a rear end, and a bottom surface; a second ski member having a front end, a rear end, and a bottom surface, said bottom surface of said second ski member being substantially coplanar with said bottom surface of said first ski member, said second ski member being positioned adjacent to said first ski member; said front end of said first ski member protruding beyond said front end of said second ski member; a slot defined between said first and second ski members; a knife blade extending through said slot, at least part of said knife blade extending beyond said respective bottom surfaces of said first and second ski members; and means for connecting said first and second ski members and said knife blade.

The surgical knife assembly provided by the invention may be utilized for eye surgery. The bottom surfaces of the ski members rest upon the outer surface of the eye as an incision is made, the depth of the incision being controlled by the relative positions of the knife blade and ski members. Due to the position of the front edge of the knife blade with respect to the front end of the second ski member, the cutting action of the blade is more easily observed by the surgeon than where the ski members both terminate at the same plane, which is conventionally well beyond the front edge of the knife blade.

DETAILED DESCRIPTION OF THE INVENTION

Figure 1:
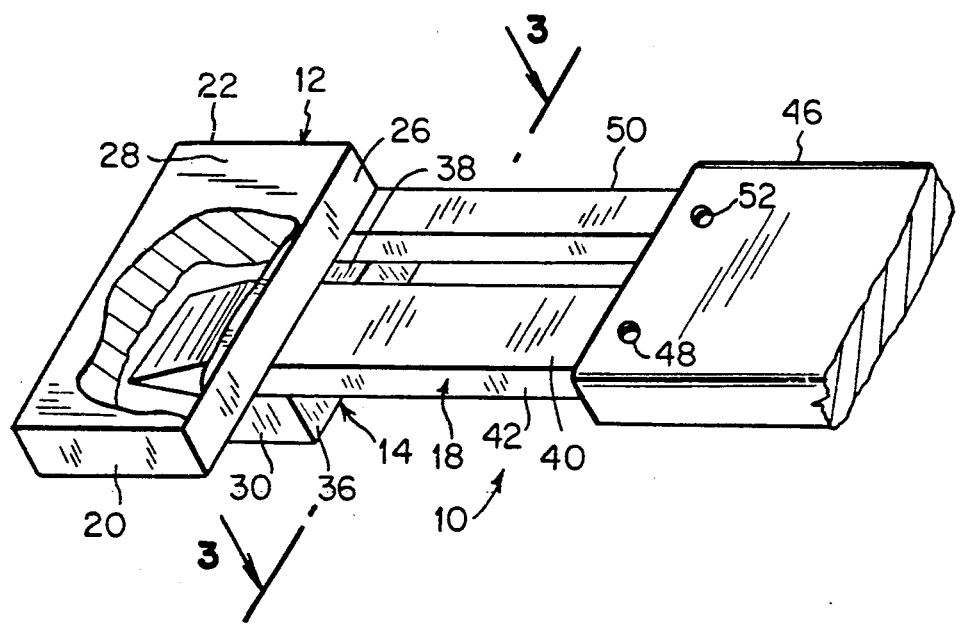
FIG. 1 is a partially cut-away, perspective view of a surgical knife assembly according to the invention.
Figure 2:
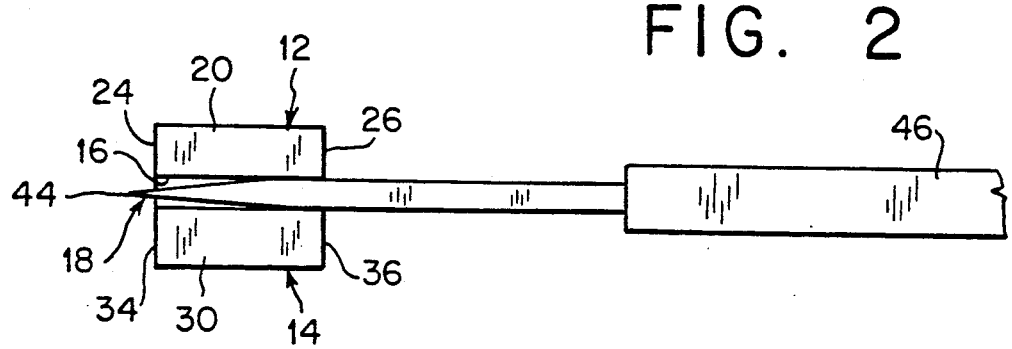
FIG. 2 is a side elevation view thereof.
Figure 3:
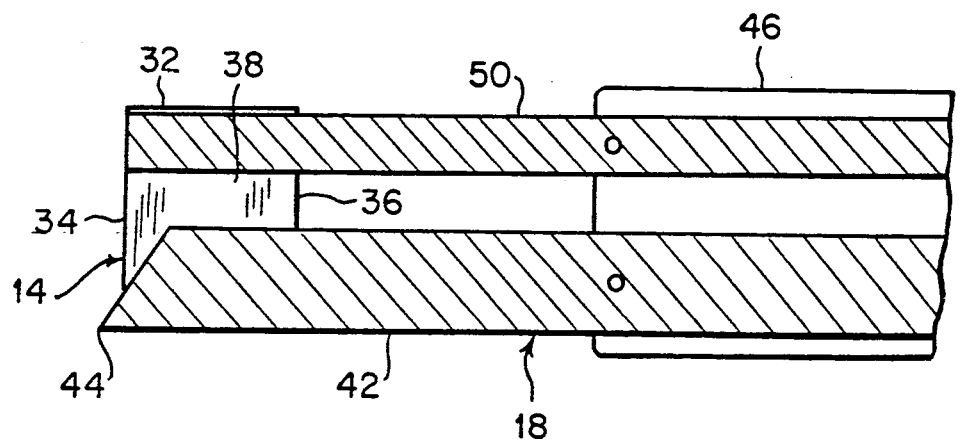
FIG. 3 is a sectional view thereof taken along line 3—3 in FIG. 1.

A surgical knife assembly 10 for making incisions into body tissue, such as eye tissue, is shown in FIGS. 1-3. The assembly 10 includes first and second adjacent ski members 12, 14 having substantially the same dimensions excepting length. A slot 16 is defined between the ski members. A knife blade 18 made from stainless steel or other suitable material extends through the slot.

The first ski member 12 includes a front end 20, a rear end 22, a flat, planar bottom surface 24, a top surface 26, and a pair of side surfaces 28. The second ski member likewise includes a front end 30, a rear end 32, a flat, planar bottom surface 34, a top surface 36, and a pair of side surfaces 38. The front end 20 of the first ski member protrudes beyond the front end 30 of the second ski member, as best shown in FIG. 1.

The knife blade 18 includes a body portion 40 having substantially the same width as the slot 16. It further includes a front edge 42 which is substantially coplanar with the front end 30 of the second ski member. The front edge may be a sharp edge if desired. This allows a surgeon to observe an incision as it is being made. The bottom edge 44 of the knife blade is a cutting edge and extends beyond the respective bottom surfaces 24, 34 of the ski members by a distance equal to the desired depth of incision. These bottom surfaces 24, 34 are substantially coplanar, and the knife blade extends substantially perpendicularly with respect to this plane.

The ski members 12, 14 and knife blade are connected directly or indirectly to a housing 46. The rear end of the knife blade extends within the housing, and is secured therein by a lock screw 48. Each of the ski members is secured to a column 50. The rear end of the column 50 extends within the housing 46, and is also secured thereto by a lock screw 52. The relative positions of the knife blade and ski members may be adjusted by loosening either lock screw and moving them with respect to the housing 46.

In use, the knife blade is adjusted with respect to the housing such that the sharp bottom edge 44 thereof projects beyond the plane defined by the bottom surfaces 24, 34. An incision is made by urging the assembly 10 towards the tissue surface until the bottom surfaces of the ski members contact the tissue surface. The knife blade is thereby maintained at the proper depth. Because the front edge 42 of the knife blade is not obscured by the second ski member, the surgeon can view the blade from the side and through the microscope to insure the incision is accurately made. As viewed from the top, it is generally preferable for the left ski member to be shorter than the right ski member as right-handed surgeons generally hold the assembly in their right hands while observing the procedure from the left "side". The opposite arrangement is generally preferable for left-handed surgeons.

While the ski members are shown herein as a pair of individual elements, it will be appreciated that they may be provided as an integral construction such as a slotted block or plate. The bottom surface of the ski members, while shown as planar, may be concave or convex to conform to a tissue surface. The front edge of the knife blade may protrude slightly beyond the front end 30 of the second ski member or be positioned slightly behind it so long as the surgeon is capable of viewing it from the side of the assembly.

Although illustrative embodiments of the present invention have been described herein with references to the accompanying drawings, it is to be understood that the invention is not limited to those precise embodiments, and that various other changes and modifications may be effected therein by one skilled in the art without departing from the scope or spirit of the invention.

What is claimed is:

1. A surgical knife assembly comprising:
   a first ski member including a front end, a rear end, and a bottom surface;
   a second ski member including a front end, a rear end, and a bottom surface, said bottom surface of said second ski member being substantially coplanar with substantially all of said bottom surface of said first ski member, said second ski member being positioned adjacent to said first ski member;
   said front end of said first ski member protruding beyond said front end of said second ski member;
   a slot defined between said first and second ski members;
   a knife blade extending through said slot, said knife blade including a cutting edge portion extending beyond said respective bottom surfaces of said first and second ski members and a front edge which is coplanar with said front end of said second ski member; and
   means for connecting said first and second ski members and said knife blade, said ski members and said knife blade being arranged such that the bottom surfaces of the respective ski members both contact the surface of a tissue when the knife blade penetrates the tissue to a selected depth.

2. A surgical knife assembly as defined in claim 1 wherein said bottom surfaces of said first and second ski members are substantially flat.

3. A surgical knife assembly as defined in claim 1 wherein said bottom surfaces of said first and second ski members are substantially flat.

4. A surgical knife assembly as defined in claim 1 wherein said knife blade extends perpendicularly with respect to said bottom surfaces of said first and second ski members.

5. A surgical knife assembly as defined in claim 1 including means for adjusting the position of said knife blade with respect to said ski members.

6. A surgical knife assembly as defined in claim 1 wherein said knife blade includes a front edge, said front edge of said knife blade being visible from at least one side of said surgical knife assembly.

7. A surgical knife assembly as defined in claim 6 wherein said front edge of said knife blade is visible from said side of said surgical knife assembly including said second ski member.

8. A surgical knife assembly as described in claim 1 including a housing, a column secured to said housing, each of said ski members being secured to said column.

9. A surgical knife assembly as described in claim 8 wherein said knife blade is secured to said housing.

10. A surgical knife assembly comprising:
    a first ski member including a front end, a rear end, and a bottom surface;
    a second ski member including a front end, a rear end, and a bottom surface, said bottom surface of said second ski member being substantially coplanar with substantially all of said bottom surface of said first ski member, said second ski member being positioned adjacent to said first ski member;
    said front end of said first ski member protruding beyond said front end of said second ski member;
    a slot defined between said first and second ski members, a major portion of the bottom surface of said second ski member being positioned directly across said slot from the bottom surface of said first ski member;
    a knife blade extending through said slot, said knife blade including a cutting edge portion extending beyond said respective bottom surfaces of said first and second ski members; and
    means for connecting said first and second ski members and said knife blade, said ski members and said knife blade being arranged such that the bottom surfaces of the respective ski members both contact the surface of a tissue when the knife blade penetrates the tissue to a selected depth.

11. A surgical knife assembly as described in claim 10 wherein the cutting edge portion of said knife blade includes a portion extending substantially parallel to the respective bottom surfaces of said ski members.

* * * * *